United States Patent
Tanaka et al.

(10) Patent No.: US 9,707,196 B2
(45) Date of Patent: Jul. 18, 2017

(54) TREATMENT AGENT AND/OR PROPHYLACTIC AGENT FOR SIDE EFFECTS OF CANCER DRUGS

(71) Applicants: SBI Pharmaceuticals Co., Ltd., Tokyo (JP); National University Corporation Kochi University, Kochi (JP)

(72) Inventors: Tohru Tanaka, Tokyo (JP); Kyoko Tsuchiya, Tokyo (JP); Masahiro Ishizuka, Tokyo (JP); Motowo Nakajima, Tokyo (JP); Hitoshi Nakagawa, Tokyo (JP); Taro Shuin, Kochi (JP); Keiji Inoue, Kochi (JP); Hideo Fukuhara, Kochi (JP); Masayuki Tsuda, Kochi (JP); Mutsuo Furihata, Kochi (JP)

(73) Assignees: SBI Pharmaceuticals Co., Ltd., Tokyo (JP); National University Corporation Kochi University, Kochi (JP)

( * ) Notice: Subject to any disclaimer, the term of this patent is extended or adjusted under 35 U.S.C. 154(b) by 0 days.

(21) Appl. No.: 14/350,520

(22) PCT Filed: Oct. 5, 2012

(86) PCT No.: PCT/JP2012/075952
§ 371 (c)(1),
(2) Date: Apr. 8, 2014

(87) PCT Pub. No.: WO2013/054756
PCT Pub. Date: Apr. 18, 2013

(65) Prior Publication Data
US 2014/0302173 A1    Oct. 9, 2014

(30) Foreign Application Priority Data

Oct. 12, 2011 (JP) ................. 2011-225382
Oct. 12, 2011 (JP) ................. 2011-225383
Mar. 30, 2012 (JP) ................. 2012-081594

(51) Int. Cl.
| | |
|---|---|
| A61K 31/195 | (2006.01) |
| A61K 31/495 | (2006.01) |
| A61K 31/505 | (2006.01) |
| A61K 31/197 | (2006.01) |
| A61K 31/28 | (2006.01) |
| A61K 33/06 | (2006.01) |
| A61K 33/26 | (2006.01) |
| A61K 33/30 | (2006.01) |
| A61K 31/221 | (2006.01) |
| A61K 31/475 | (2006.01) |
| A61K 31/513 | (2006.01) |
| A61K 31/519 | (2006.01) |
| A61K 33/24 | (2006.01) |
| A61K 45/06 | (2006.01) |
| A61K 31/4745 | (2006.01) |
| A61K 31/555 | (2006.01) |

(52) U.S. Cl.
CPC .......... A61K 31/197 (2013.01); A61K 31/221 (2013.01); A61K 31/28 (2013.01); A61K 31/475 (2013.01); A61K 31/4745 (2013.01); A61K 31/513 (2013.01); A61K 31/519 (2013.01); A61K 31/555 (2013.01); A61K 33/06 (2013.01); A61K 33/24 (2013.01); A61K 33/26 (2013.01); A61K 33/30 (2013.01); A61K 45/06 (2013.01)

(58) Field of Classification Search
CPC .............. A61K 31/197; A61K 31/4745; A61K 31/513; A61K 31/519; A61K 31/555; A61K 33/24; A61K 33/26; A61K 31/221; A61K 31/28; A61K 31/475; A61K 33/06; A61K 33/30; A61K 45/06
USPC ........................ 514/249, 274, 283, 502, 561
See application file for complete search history.

(56) References Cited

U.S. PATENT DOCUMENTS

| | | | |
|---|---|---|---|
| 8,093,425 B2* | 1/2012 | Koya ............ | A61K 45/06 562/899 |
| 9,018,257 B2* | 4/2015 | Rephaeli ....... | A61K 41/0061 514/547 |
| 2004/0234555 A1 | 11/2004 | Oshida et al. | |
| 2008/0026075 A1 | 1/2008 | Kondo et al. | |
| 2014/0256806 A1 | 9/2014 | Tanaka et al. | |
| 2014/0288172 A1 | 9/2014 | Tanaka et al. | |

(Continued)

FOREIGN PATENT DOCUMENTS

| | | |
|---|---|---|
| JP | 2003-040770 A | 2/2003 |
| JP | 2006-069963 A | 3/2006 |

(Continued)

OTHER PUBLICATIONS

Fijan et al., Photodynamic therapy of epithelial skin tumours using delta-aminolaevulinic acid and desferrioxamine, British Journal of Dermatology, 133; 282-288, 1995.*

(Continued)

*Primary Examiner* — My-Chau T Tran
(74) *Attorney, Agent, or Firm* — Osha Liang LLP (57) ABSTRACT

A method for treating side effects of anticancer agent includes administering to a subject in need thereof a prophylactic and/or therapeutic agent containing a therapeutically effective amount of a compound shown by the following Formula (I):

$$R^1\text{—NHCH}_2\text{COCH}_2\text{CH}_2\text{COOR}^2 \qquad (I)$$

wherein $R^1$ represents a hydrogen atom or an acyl group, and $R^2$ represents a hydrogen atom, a linear or branched alkyl group, a cycloalkyl group, an aryl group, or an aralkyl group, or a salt thereof.

4 Claims, 6 Drawing Sheets

(56) References Cited

U.S. PATENT DOCUMENTS

| | | | |
|---|---|---|---|
| 2014/0288173 A1 | 9/2014 | Tanaka et al. | |
| 2014/0302173 A1 | 10/2014 | Tanaka et al. | |

FOREIGN PATENT DOCUMENTS

| | | | |
|---|---|---|---|
| JP | 2009/298739 A | 12/2009 | |
| JP | 2011-016753 A | 1/2011 | |
| JP | 5818906 B2 | 11/2015 | |
| TW | 201317206 A | 5/2013 | |
| TW | 201318623 A | 5/2013 | |
| TW | 201320995 A | 6/2013 | |
| WO | 00/54795 A1 | 9/2000 | |
| WO | 2007/132234 A1 | 11/2007 | |
| WO | 2010/065079 A2 | 6/2010 | |

OTHER PUBLICATIONS

Flock et al., Photofrin and 5-Aminolevulinic Acid Permeation Through Oral Mucosa in Vitro, SPIE, 2133:194-199, 1994.*

International Search Report for corresponding International Application No. PCT/JP2012/075952, mailed Dec. 18, 2012, with English translation (4 pages).

Levi, J. A., et al., "Haemolytic anaemia after cisplatin treatment"; British Medical Journal (Clinical Research Edition), vol. 282, No. 6281, Jun. 20, 1981; pp. 2003-2004.

Appenroth, D., et al., "Protective effects of vitamin E and C on cisplatin nephrotoxicity in developing rats"; Arch. Toxicol., vol. 71, No. 11, 1997; pp. 677-683.

Bogin, E., et al., "Changes in Serum, Liver and Kidneys of Cisplatin-Treated Rats; Effects of Antioxidants"; Eur. J. Clin. chem. Clin. Biochem., vol. 32, No. 11, 1994; pp. 843-851.

Rao, Mahadev, et al., "In Vitro and In Vivo Effects of Phenolic Antioxidants against Cisplatin-Induced Nephrotoxicity"; J. Biochem., vol. 125, No. 2; pp. 383-390.

EPO Communication ("Office Action") dated Mar. 10, 2015, issued by the European Patent Office in corresponding European Patent Application No. EP-12839452.5 (1 page), with an Extended European Search Report dated Feb. 25, 2015 (5 pages).

Database WPI, Week 201003; Thomson Scientific, London, GB; AN 2009-S70615; XP002736406 (3 pages). [Corresponds to JP-2009298739].

Office Action issued in corresponding Taiwanese Application No. 101137456 dated Mar. 28, 2016 (6 pages).

J. Taïeb, et al.; "Intensive Systemic Chemotherapy Combined With Surgery for Metastatic Colorectal Cancer: Results of a Phase II Study" Journal of clinical Oncology.; vol. 23, No. 3, pp. 502-509; Jan. 2005 (8 pages).

Office Action issued in Japanese Application No. 2015-189250; Dated Jul. 20, 2016 (9 pages).

* cited by examiner

TREATMENT AGENT AND/OR PROPHYLACTIC AGENT FOR SIDE EFFECTS OF CANCER DRUGS

TECHNICAL FIELD

The present invention relates to a prophylactic and/or therapeutic agent for side effects of anticancer agent. More specifically, the present invention relates to a prophylactic and/or therapeutic agent for side effects of anticancer agent comprising ALAs.

BACKGROUND ART

Although anticancer agents are one of the three major cancer therapies along with surgery and radiation therapy, it often causes severe side effects. In general, potent anticancer agents have stronger side effects. Accordingly, physicians and patients are forced to make a rough choice in regards to the use of anticancer agents.

From such background, several methods for alleviating the side effects of anticancer agent have been proposed. For example, a method of prescribing a Chinese herbal medicine such as Shiquan Dabu teapills, a method of controlling the administration timing of the anticancer agent based on chronobiology, and a method of performing a large-scale transfusion during anticancer agent administration to protect the organs are being performed. However, the effect of alleviating the side effects of anticancer agent is still insufficient even with these methods. In addition, hospitalization is necessary for performing nighttime infusion or large-scale transfusion etc., causing a large burden in both physical and medical economical terms.

Moreover, as a method for alleviating the side effects of anticancer agent, development of agents that allow reduction of side effects are also under progress. As such agent, edaravone which is a cerebral ischemic therapeutic was acknowledged to have an alleviating action on the side effects of cisplatin on renal function, thus gathering much attention. However, this agent was found during development to have severe side effects including death caused by renal failure, and was not put on the market.

In the first place, what are the actions of anticancer agents? What is the mechanism of the side effects of anticancer agent to occur? Numerous anticancer agents already exist, and the action mechanisms of anticancer agents are being researched. Many anticancer agents show anticancer action by inhibiting DNA replication or cell cycle. Such anticancer agents show a more potent growth suppression effect on cancer cells with faster growth. On the other hand, however, because it shows similar growth suppression effect on normal cells, it also shows damage to hair roots and the intestinal tract which have fast growth among normal cells. This causes the side effects of anticancer agent.

Moreover, a type of anticancer agents suppresses and kills cancer by producing reactive oxygen species. On the other hand, the reactive oxygen produced by the anticancer agent will cause harm to normal cells not to a small extent, and this causes side effects. Administration of an antioxidant is conceivable as a method for alleviating this type of anticancer agent side effect. However, it is obvious that an antioxidant will attenuate the essential anticancer effect of the anticancer agent. Further, even if the antioxidant can alleviate this type of anticancer agent side effect, it will not be able to alleviate other types of anticancer agent side effects.

As described above, potent anticancer agents have stronger side effects. To put it conversely, anticancer agents with little side effects do not have much anticancer effect. In addition, agents that suppress the side effects of anticancer agent will also suppress the anticancer effect of anticancer agent. Molecular target drugs appeared with flourish as ideal anticancer agents to escape this dilemma. However, even without seeing the case of interstitial pneumonitis with Iressa, molecular target drugs have also not escaped from the problems of their side effects. Moreover, molecular target drugs are extremely expensive without exception.

From such background, the development of a truly effective prophylactic and/or therapeutic agent for side effects of anticancer agent has been yearned by physicians and patients. The development of a truly effective prophylactic and/or therapeutic agent for side effects of anticancer agent has also been yearned as a social demand carrying the burden of expensive healthcare cost.

SUMMARY OF THE INVENTION

Problems to be Solved by the Invention

The object of the present invention is to provide an effective prophylactic and/or therapeutic agent for side effects of anticancer agent.

Means for Solving the Problems

ALA herein means 5-aminolevulinic acid. ALA is also referred to as δ-aminolevulinic acid, and is a type of amino acid. ALA is an in vivo endogenous substance known to be the precursor of heme. Various bioactivities are known for ALA, and it is broadly employed in the diagnosis of e.g. cancer, or in the therapeutic field for photokinetic therapy (PDT, Photo Dynamic Therapy) and photokinetic diagnosis (PDD, Photo Dynamic Diagnosis). It is known that although ALA is a common precursor of heme-based compounds, in cancer cells, heme is not produced even when ALA is administered, and protoporphyrin IX (PPIX) which is the precursor of heme-based compounds is accumulated. PPD is possible because fluorescence is emitted when light is irradiated on the accumulated PPIX. Further, in the presence of oxygen, PDT is possible because reactive oxygen is produced when light is irradiated on the accumulated PPIX. In other words, ALA is merely related to anticancer agent as a sensitizer of PDT, and the use of ALA as a prophylactic and/or therapeutic agent for side effects of anticancer agent is completely unanticipated.

Although ALA is known to improve the metabolism of sugars and lipids, there are no reports stating that the side effects of anticancer agent are related to the metabolism of sugars and lipids, and it cannot be envisioned from existing information that ALA is effective for the prevention or therapy of the side effects of anticancer agent.

The present inventors, after repeated extensive investigations, established a prophylactic and/or therapeutic agent for side effects of anticancer agent comprising ALAs to complete the present invention (though elucidation of the exact mechanism of why ALAs are effective in alleviating the side effects of anticancer agent is a future scientific task.).

In other words, the present invention relates a prophylactic and/or therapeutic agent for side effects of anticancer agent, characterized in that it comprises a compound shown by the following Formula (I):

$$R^1-NHCH_2COCH_2CH_2COOR^2 \qquad (I)$$

(wherein $R^1$ represents a hydrogen atom or an acyl group, and $R^2$ represents a hydrogen atom, a linear or branched alkyl group, a cycloalkyl group, an aryl group, or an aralkyl group) or a salt thereof.

The prophylactic and/or therapeutic agent of the present invention for side effects of anticancer agent may further contain one or two or more metals. Such metal may be selected from the group consisting of iron, magnesium, and zinc.

Moreover, said side effects of anticancer agent may be any side effect of anticancer agent. For example, said side effects of anticancer agent may be a side effect related to the kidney, a side effect related to skin symptoms, a side effect related to general symptoms, or a side effect related to the gastrointestinal system. Said side effects of anticancer agent may also be any and all side effects of anticancer agent excluding the side effects related to the blood or the bone marrow.

The prophylactic and/or therapeutic agent of the present invention for side effects of anticancer agent can also be used in combination with an anticancer agent.

The present invention also further relates to a medicine for cancer therapy consisting of a combination of (1) a prophylactic and/or therapeutic agent for side effects of anticancer agent comprising a compound shown by the above Formula (I) and (2) an anticancer agent. These agents can be administered simultaneously or at different times.

Effects of the Invention

The present invention provides a prophylactic and/or therapeutic agent for side effects of anticancer agent. Therapy in the present invention comprises not only completely removing the side effects of anticancer agent, but also improving the symptom of the side effects. Similarly, prevention comprises not only completely stopping the symptoms of the side effects from occurring, but also allowing the symptoms of the side effects which will have occurred without administering the prophylactic agent of the present invention to bemilder. Superior prophylactic and/or therapeutic effect for side effects of anticancer agent can be obtained by using the agent of the present invention.

Moreover, by administering the prophylactic and/or therapeutic agent of the present invention for side effects of anticancer agent, for example, administration of a standard amount of anticancer agent to a patient may become possible even when the anticancer agent cannot be administered at all or a standard amount of anticancer agent cannot be administered to the said patient due to severe side effects. Accordingly, by administering the prophylactic and/or therapeutic agent of the present invention for side effects of anticancer agent, the inherent effect of the anticancer agent can be drawn at its maximum, and not only the effect of improving the QOL of the patient but also the effect of extending the patient's life may be expected.

Accordingly, the agent of the present invention is not only beneficial for the patient receiving the anticancer agent therapy, but can also reduce the social loss due to the side effects of anticancer agent.

DESCRIPTION OF EMBODIMENTS

The prophylactic and/or therapeutic agent of the present invention for side effects of anticancer agent is not particularly limited as long as it is a prophylactic and/or therapeutic agent for side effects of anticancer agent containing ALAs. The agent of the present invention can be taken before the anticancer agent therapy, simultaneously with the anticancer agent therapy, after the anticancer agent therapy, or after the occurrence of the anticancer agent side effects, as appropriate according to the embodiment.

By employing the prophylactic and/or therapeutic agent of the present invention for side effects of anticancer agent, the side effects of anticancer agent are alleviated, and thereby in some cases can allow increase in the administration dose of anticancer agent.

The prophylactic and/or therapeutic agent of the present invention for side effects of anticancer agent can also be used in combination with an anticancer agent, for example as a drug combination, or used as a kit.

The anticancer agent in the present invention is not particularly limited. A non-limiting example of such an anticancer agent can include platinum-containing antitumor agent (such as cisplatin).

The side effects of anticancer agent in the present invention refer to the physical deficiency in general due to an anticancer agent. The side effects of anticancer agent are various. Non-limiting examples of such side effects can include (1) side effects related to blood or bone marrow such as decrease of hemoglobin, hemolysis, and anemia, (2) side effects related to general symptoms such as weakness, malaise, and weight loss, (3) side effects related to skin symptoms such as hair loss and rash, (4) side effects related to the gastrointestinal system such as nausea, retching, constipation, and diarrhea, and (5) side effects related to the kidney (nephrotoxicity) such as renal failure.

The compound employed as the prophylactic and/or therapeutic agent of the present invention for side effects of anticancer agent is ALAs. ALAs herein refer to ALA or a derivative thereof or a salt thereof.

Examples of ALA derivatives can include compounds represented by the following Formula (I). In Formula (I), $R^1$ represents a hydrogen atom or an acyl group, and $R^2$ represents a hydrogen atom, a linear or branched alkyl group, a cycloalkyl group, an aryl group, or an aralkyl group. In Formula (I), ALA corresponds to the case where $R^1$ and $R^2$ are hydrogen atoms.

$$R^1-NHCH_2COCH_2CH_2COOR^2 \qquad (I)$$

ALAs may be those that act in vivo as an active ingredient as the ALA of Formula (I) or a derivative state thereof, and can also be administered as a prodrug (precursor) that is degraded by an in vivo enzyme.

The acyl group in $R^1$ of Formula (I) can include a linear or branched alkanoyl group having 1 to 8 carbons such as formyl, acetyl, propionyl, butyryl, isobutyryl, valeryl, isovaleryl, pivaloyl, hexanoyl, octanoyl, and benzylcarbonyl groups, and an aroyl group having 7 to 14 carbons such as benzoyl, 1-naphthoyl, and 2-naphthoyl groups.

The alkyl group in $R^2$ of Formula (I) can include a linear or branched alkyl group having 1 to 8 carbons such as methyl, ethyl, propyl, isopropyl, butyl, isobutyl, sec-butyl, tert-butyl, pentyl, isopentyl, neopentyl, hexyl, heptyl, and octyl groups.

The cycloalkyl group in $R^2$ of Formula (I) can include a cycloalkyl group having 3 to 8 carbons with saturated or possibly partially unsaturated bonds, such as cyclopropyl, cyclobutyl, cyclopentyl, cyclohexyl, cycloheptyl, cyclooctyl, cyclododecyl, and 1-cyclohexenyl groups.

The aryl group in $R^2$ of Formula (I) can include an aryl group having 6 to 14 carbons such as phenyl, naphthyl, anthryl, and phenanthryl groups.

The aralkyl group in $R^2$ of Formula (I) can include the same exemplification as the above aryl groups for the aryl moiety and the same exemplification as the above alkyl groups for the alkyl moiety, specifically, an aralkyl group having 7 to 15 carbons such as benzyl, phenethyl, phenylpropyl, phenylbutyl, benzhydryl, trityl, naphthylmethyl, and naphthylethyl groups.

Preferred ALA derivatives include compounds where $R^1$ is e.g. a formyl, an acetyl, a propionyl, or a butyryl group. Preferred ALA derivatives also include compounds where the above $R^2$ is e.g. a methyl, an ethyl, a propyl, a butyl, or a pentyl group. Preferred ALA derivatives also include compounds where the combination of the above $R^1$ and $R^2$ is each a combination of (formyl and methyl), (acetyl and methyl), (propionyl and methyl), (butyryl and methyl), (formyl and ethyl), (acetyl and ethyl), (propionyl and ethyl), or (butyryl and ethyl).

Among ALAs, examples of a salt of ALA or a derivative thereof can include a pharmaceutically acceptable acid addition salt, a metal salt, an ammonium salt, and an organic amine addition salt. Examples of an acid addition salt can be, for example, each of inorganic acid salts such as hydrochloride, hydrobromide, hydroiodide, phosphate, nitrate, and sulfate salts, and each of organic acid addition salts such as formate, acetate, propionate, toluenesulfonate, succinate, oxalate, lactate, tartrate, glycolate, methanesulfonate, butyrate, valerate, citrate, fumarate, maleate, and malate salts. Examples of a metal salt can be each of alkali metal salts such as lithium, sodium, and potassium salts, each of alkaline earth metal salts such as magnesium and calcium salts, and each of metal salts such as aluminum and zinc salts. Examples of an ammonium salt can be alkyl ammonium salts such as ammonium and tetramethylammonium salts. Examples of an organic amine salt can include each of triethylamine, piperidine, morpholine, and toluidine salts. These salts can also be employed as a solution at the time of use.

Among the above ALAs, the most preferred are ALA and various esters such as ALA methyl ester, ALA ethyl ester, ALA propyl ester, ALA butyl ester, and ALA pentyl ester, as well as hydrochloride, phosphate, and sulfate salts thereof. Among these, ALA hydrochloride and ALA phosphate salts can be exemplified as particularly preferable.

The above ALAs can be produced by e.g. a well-known method such as chemical synthesis, microorganic production, and enzymatic production. The above ALAs may also form a hydrate or a solvate, and ALAs can be employed alone or in an appropriate combination of two or more.

The prophylactic and/or therapeutic agent of the present invention for side effects of anticancer agent is preferably those further containing a metal in a range that does not cause symptoms due to excess. A metal compound can be favorably employed as said metal, as long as it does not adversely affect the advantages of the present invention. The metal according to the present invention can include iron, magnesium, zinc, nickel, vanadium, cobalt, copper, chromium, and molybdenum, although iron and zinc are preferred.

Examples of an iron compound can include ferrous citrate, sodium ferrous citrate, iron sodium citrate, iron ammonium citrate, ferric pyrophosphate, heme iron, iron dextran, iron lactate, ferrous gluconate, iron sodium diethylenetriaminepentaacetate, iron ammonium diethylenetriamine pentaacetate, iron sodium ethylenediaminetetraacetate, iron ammonium ethylenediaminepentaacetate, triethylenetetramine iron, iron sodium dicarboxymethylglutamate, iron ammonium dicarboxymethylglutamate, lactoferrin iron, transferrin iron, ferric chloride, iron sesquioxide, sodium iron chlorophyllin, ferritin iron, ferrous fumarate, ferrous pyrophosphate, saccharated iron oxide, iron acetate, iron oxalate, ferrous succinate, iron sodium succinate citrate, iron sulfate, and iron glycine sulfate. Among these, ferrous citrate and sodium ferrous citrate are preferred.

Zinc compounds can include zinc chloride, zinc oxide, zinc nitrate, zinc carbonate, zinc sulfate, zinc diammonium diethylenetriaminepentaacetate, zinc disodium ethylenediaminetetraacetate, zinc protoporphyrin, zinc-containing yeast, and zinc gluconate.

One or two or more of each of the above metals can be employed, and the administration dose of the metal can include a molar ratio of 0.01 to 10-folds, preferably 0.1 to 5-folds, and more preferably 0.2 to 2-folds relative to the administration dose of ALAs.

The ALAs and the metal contained in the prophylactic and/or therapeutic agent of the present invention for side effects of anticancer agent can be administered as a composition comprising the ALAs and the metal or as each alone, but simultaneous administration is preferred even when they are each administered alone. However, it may not need to be strictly simultaneous, but may be performed without a substantial interval between the two so that the administration of the ALAs and the metal can show an additive or synergistic effect.

Examples of the administration route for the prophylactic and/or therapeutic agent of the present invention for side effects of anticancer agent can include oral administration including sublingual administration, or parenteral administration such as inhalation administration, intravenous administration including infusion, transdermal administration by e.g. a poultice, suppository, or administration by forced enteral nutrient employing a nasogastric tube, a nasointestinal tube, a gastrostomy tube, or an enterostomy tube, but oral administration is used in general.

The administration subject is typically a human, but a non-human animal such as a pet, an experiment animal, and a farm animal may also be included.

The dosage form of the prophylactic and/or therapeutic agent of the present invention for side effects of anticancer agent can be appropriately determined depending on the above administration routes, and can include, for example, injections, infusions, tablets, capsules, fine granules, powders, solutions, liquors dissolved e.g. in a syrup, poultices, and suppositories.

In order to prepare the prophylactic and/or therapeutic agent of the present invention for side effects of anticancer agent, a pharmaceutically acceptable carrier, excipient, diluent, additive, disintegrant, binder, coating, lubricant, gliding agent, glossing agent, flavoring agent, sweetening agent, solubilizer, solvent, gelling agent, and nutrient etc. can be added as necessary, specific examples of which can be water, saline, animal fat and oil, vegetable oil, lactose, starch, gelatin, crystalline cellulose, gum, talc, magnesium stearate, hydroxypropylcellulose, polyalkylene glycol, polyvinyl alcohol, and glycerin. When the prophylactic and/or therapeutic agent of the present invention for side effects of anticancer agent is prepared as an aqueous solution, care must be taken so that the aqueous solution will not be alkaline in order to prevent the degradation of ALAs. If it becomes alkaline, degradation can also be prevented by removing oxygen.

The amount/frequency/duration of the prophylactic and/or therapeutic agent of the present invention for side effects of anticancer agent will vary according to the age, weight, and symptoms etc. of the person that is to utilize the prophylactic and/or therapeutic agent of the present invention for side effects of anticancer agent. Examples of the preferred administration dose can include 4 µmol to 13100 µmol, preferably 7 µmol to 4400 µmmol, more preferably 13 µmol to 3100 µmol, and further preferably 20 µmol to 880 µmol per one adult. Note that the above preferred administration dose range are exemplary and are not limiting.

The administration timing of the prophylactic and/or therapeutic agent of the present invention for side effects of anticancer agent is most desirably continuously administering of agent of the present invention from at least three days or more before starting the administration of the anticancer agent, and continuing the administration of the agent of the present invention even during the duration of therapy by anticancer agent. However, a certain effect can be expected even if administration of the agent of the present invention is started when starting the administration of the anticancer agent, and continuing the administration of the agent of the present invention during the duration of therapy by anticancer agent. Moreover, a certain effect can be expected even if the agent of the present invention is administered only during the period before starting the administration of the anticancer agent.

Moreover, by administering the prophylactic and/or therapeutic agent of the present invention for side effects of anticancer agent, for example, administration of a standard amount of anticancer agent to a patient may become possible even when the anticancer agent cannot be administration at all or a standard amount of anticancer agent cannot be administered to the said patient due to severe side effects. Accordingly, by administering the prophylactic and/or therapeutic agent of the present invention for side effects of anticancer agent, the inherent effect of the anticancer agent can be drawn at its maximum, and not only the effect of improving the QOL of the patient but also the effect of extending the patient's life may be expected.

The prophylactic and/or therapeutic agent of the present invention for side effects of anticancer agent can also be used in combination with other existing prophylactic and/or therapeutic agents for side effects of anticancer agent. Examples of existing prophylactic and/or therapeutic agents for side effects of anticancer agent include a large-scale administration of an electrolyte by infusion or Chinese herbal medicines such as Shiquan Dabu teapills. Since the mechanisms of these agents and ALA regarding the prophylactic and/or therapeutic agent for side effects of anticancer agent are each thought to be fundamentally different, additive, and in some cases synergistic effect can be expected.

Unless otherwise defined, the terms used herein are employed to describe a particular embodiment and do not intend to limit the invention.

In addition, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms.) have the same meaning as that broadly recognized by those skilled in the art of the technology to which the present invention belongs. Unless explicitly defined otherwise, the terms used herein should be construed to have meanings consistent with those herein and in the related technical fields, and are not to be construed as idealized or excessively formal meanings.

The present invention will now be more specifically described by Examples, but the technological scope of the present invention is not limited to these exemplifications.

EXAMPLES

Example 1: Effect of Reducing the Side Effects of ALA Administration on Various Side Effects Accompanying Cisplatin Administration In order to verify the effect of reducing the side effects by administration of ALAs on side effects arising from anticancer agent administration, cisplatin and ALA were administered to rats, and the influence on rats was verified.

Forty-four 6 weeks-old SD rats (male) were purchased from Japan SLC, Inc. They were used for experiments after conditioning for 7 days after purchase.

The experiment duration was a total of 16 days, and experiment groups were divided into the following 5 groups I to V according to the ALA administration condition. In all experiment groups except the negative control group (Group I), cisplatin (CDDP) was administered on Day 6 from the start of experiment. CDDP administration dose was 8.0 mg/kg of body weight, and each rat was intraperitoneally administered. Saline was administered instead of cisplatin to Group I as the negative control group. ALA was also administered to Groups III, VI, and V according to the following schedule. On the other hand, no ALA was administered to the positive control group (Group II). ALA administration to Groups III, IV, and V was performed by daily oral administration of 10 mg/kg of body weight of ALA hydrochloride salt+15.7 mg/kg of body weight of sodium ferrous citrate (dissolved in distilled water and sodium bicarbonate).

(ALA Administration Conditions of Groups I to V)

Group I (negative control group): Saline was administered on Day 6 from the start of experiment. They were otherwise kept as usual. n=4

Group II (positive control group): CDDP was administered on Day 6 from the start of experiment. They were otherwise kept as usual. n=10

Group III ("pre-administration group"): ALA was administered for a total of 5 days from the starting day of experiment to Day 5. CDDP was also administered on Day 6. They were otherwise kept as usual. n=10

Group IV ("post-administration group"): On Day 6 from the start of experiment, ALA was administered, and then CDDP was administered. ALA was also administered for 10 days from Day 6 to Day 15. They were otherwise kept as usual. n=9

Group V ("full administration group"): ALA was administered for 15 days from the starting day of experiment to Day 15. On Day 6, ALA was administered, and then CDDP was administered. n=9

Blood was collected every two days for 15 days from the starting day of experiment to Day 15. Observation of hair luster, stool state, and activity of rats was also carried out. Each rat was also dissected on Day 16, and the kidney was resected. Kidney sections were prepared after resection, and observed under a microscope after HE staining.

Figure 1:
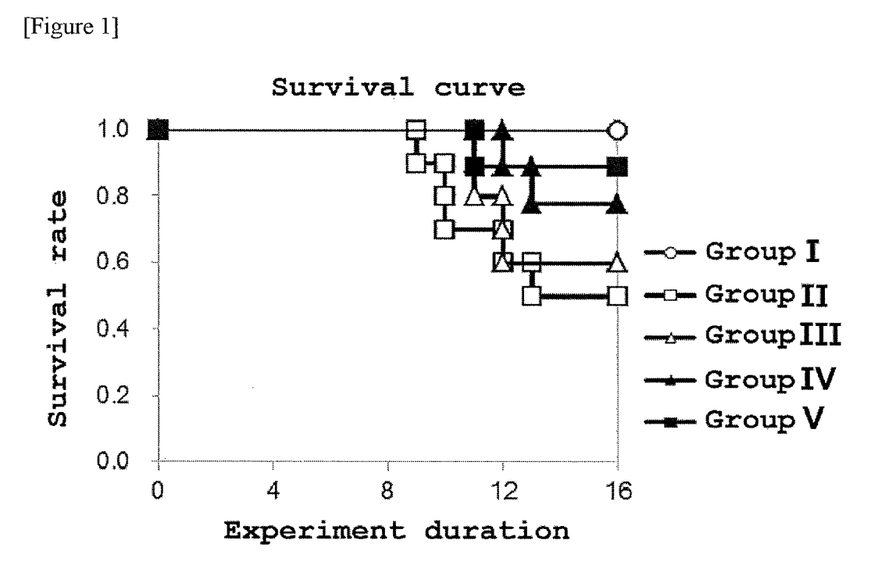
FIG. 1 is the graph showing the transition of survival rate according to administration conditions, when 6 weeks-old SD rats are administered cisplatin and ALA by 5 administration conditions.

The rat survival rate of each experiment group for the duration of this experiment is shown in FIG. 1. As shown in FIG. 1, in the positive control group (Group II), reduction in the survival rate was seen on Day 9 from the starting day of experiment due to the side effects of anticancer agent. In contrast, in groups administered with ALA (Groups III, IV, and V), the timing of the start of reduction in the survival rate was delayed due to side effects from anticancer agent. It is also shown in groups administered with ALA (Groups III, IV, and V) that reduction in the survival rate until Day 16 could be suppressed. The "full administration group" administered with ALA throughout the duration of experiment (Group V) had the highest survival rate. However, a certain suppression effect on the side effects of anticancer agent was shown even for the "pre-administration group" (Group III) or the "post-administration group" (Group IV). Accordingly, reliable therapeutic and prophylactic effects by ALA administration were shown in regards to reduction in the survival rate due to the side effects of anticancer agent.

Figure 2:
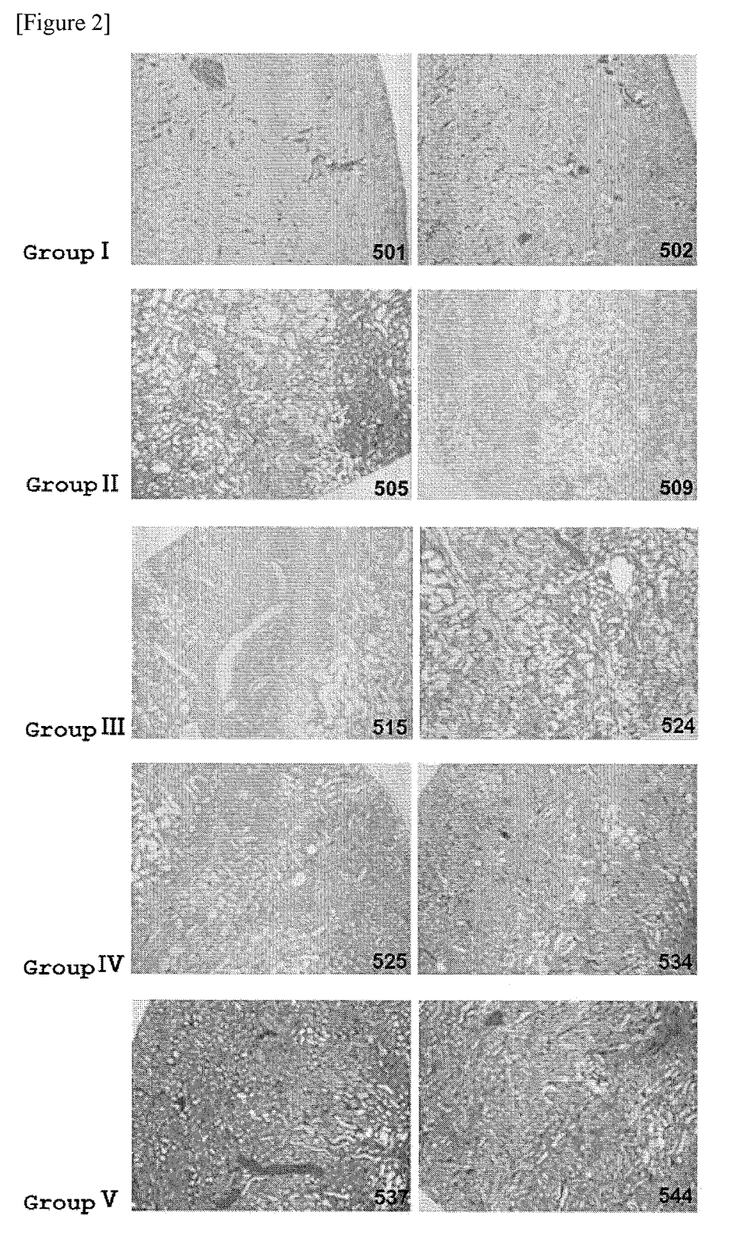
FIG. 2 is the HE staining image of the kidney on Day 16 from the starting day of experiment, when 6 weeks-old SD rats are administered cisplatin and ALA by 5 administration conditions.

After fixing the kidney resected by dissection from each rat on Day 16 with formalin, sections were prepared, and the state of the kidney was verified by HE staining. The HE staining images of the kidney are shown in FIG. 2. As shown in FIG. 2, administration of ALA has alleviated the damage to the kidney due to the side effects of anticancer agent. The "full administration group" administered with ALA throughout the duration of experiment (Group V) was the most effective. However, a certain effect was shown even in the "pre-administration group" (Group III) and the "post-administration group" (Group IV). Accordingly, reliable therapeutic and prophylactic effects were shown in regards to the damage to the kidney due to the side effects of anticancer agent.

The evaluation regarding hair luster, stool state, and activity of each rat in Groups I to V is shown in the following Table 1. Side effects were strongly observed from Day 9 to Day 13 from the starting day of experiment. Accordingly, the state on Days 9, 11, and 13 were scored and evaluated. Hair luster here evaluates the side effect related to skin symptoms. Stool state evaluates the side effect related to the gastrointestinal system. Activity evaluates the side effect related to general symptoms, in particular evaluates the side effect related to malaise.

Each item was evaluated for each mouse by the following criteria, and is the numerical value of the sum of the three days (Days 9, 11, and 13) divided by the number of evaluation subject mice.

(Hair Luster)

5: Very good, 4: ordinarily state, 3: slightly poor, 2: poor, and 1: death (Stool State)

5: Ordinarily stool, 4: small amount of stool, 3: slight diarrhea, 2: diarrhea, and 1: death (Activity)

5: Ordinarily state, 4: weak movement, 3: slight movement, 2: no movement, and 1: death (Overall Evaluation)

5: Very good, 4: ordinarily state, 3: slightly poor, 2: poor, and 1: death

TABLE 1

|  | Final evaluation | | | |
| --- | --- | --- | --- | --- |
|  | Hair luster | Stool state | Activity | Overall evaluation |
| Group I | 13.00 | 15.00 | 15.00 | 12.00 |
| Group II | 7.80 | 9.30 | 7.30 | 7.10 |
| Group III | 8.10 | 8.90 | 8.10 | 7.50 |
| Group IV | 8.89 | 10.78 | 9.56 | 8.78 |
| Group V | 11.33 | 13.33 | 11.33 | 9.67 |

As apparent from Table 1, ALA administration was shown to have an alleviating action on various side effects caused by anticancer agent. The "full administration group" administered with ALA throughout the duration of experiment (Group V) showed the most preferable result. However, a certain effect was shown even in the "pre-administration group" (Group III) or the "post-administration group" (Group IV). Accordingly, reliable therapeutic and prophylactic effects by ALA administration were shown in regards to the side effects of anticancer agent.

Example 2: Effect of Reducing the Side Effects of ALA Administration on Side Effects on the Kidney Accompanying Cisplatin Administration In order to verify the effect of reducing the side effects by administration of ALAs on side effects on the kidney (nephrotoxicity) by anticancer agent administration, cisplatin and ALA were administered to rats, and the influence on rat serum creatinine, urea nitrogen value (BUN), and urine protein was verified. Serum creatinine and urea nitrogen value (BUN) were measured from blood samples. Moreover, urine protein was measured from urine samples.

Weight loss which is a side effect on general symptoms as well as a side effect related to the gastrointestinal system was also observed at the same time.

Forty-six 6 weeks-old SD rats (male) were purchased from Japan SLC, Inc. They were conditioned for 7 days after purchase. Body weight measurement, blood collection, and urine collection of each rat were performed at the end of the conditioning period. The experiment was started on the next day with 44 rats. Two individuals that had poor serum creatinine, urea nitrogen value (BUN), and urine protein value at the measurement after conditioning were excluded from the experiment.

In this experiment, experiment groups were divided into the following 4 groups I to IV according to the ALA administration condition. The experiment was otherwise performed similarly to Example 1.

Group I (negative control group): Saline was administered on Day 6 from the start of experiment. They were otherwise kept as usual. n=8

Group II (positive control group): CDDP was administered on Day 6 from the start of experiment. They were otherwise kept as usual. n=14

Group III ("post-administration group"): On Day 6 from the start of experiment, ALA was administered, and then CDDP was administered. ALA was also administered for 10 days from Day 6 to Day 15. They were otherwise kept as usual. n=10

Group IV ("full administration group"): ALA was administered for 15 days from the starting day of experiment to Day 15. On Day 6, ALA was administered, and then CDDP was administered. n=11

The body weight of each rat was measured, and blood and urine collection was carried out on starting day of experiment, Days 6, 7, 9, 11, 13, and 15. The collected blood samples were used for measuring serum creatinine and urea nitrogen value (BUN). In addition, the collected urine samples were used for measuring urine protein. Each rat was also dissected on Day 16, and the kidney was resected and observed.

Figure 3:
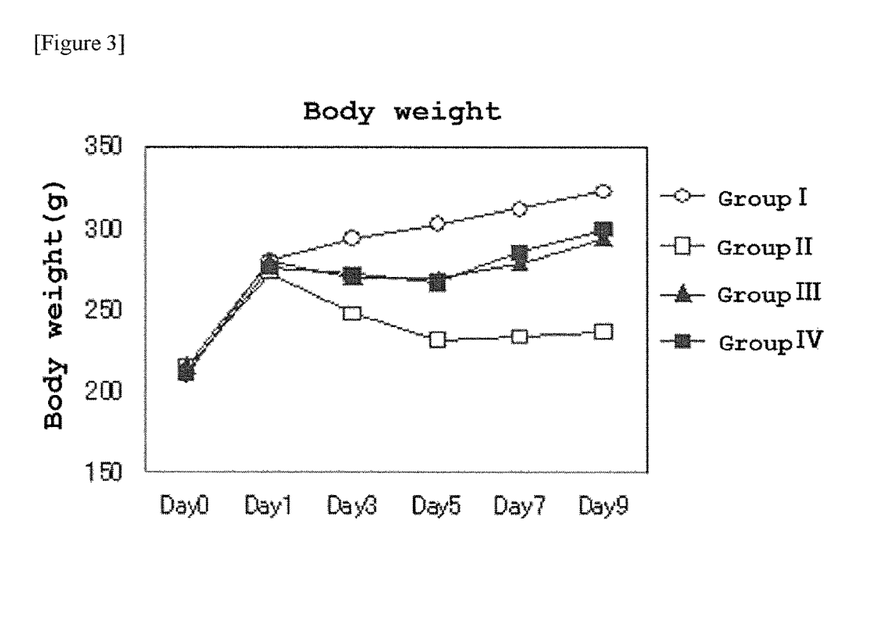
FIG. 3 is the graph showing the transition of body weight according to administration conditions, when 6 weeks-old SD rats are administered cisplatin and ALA by 4 administration conditions.

The rat body weight change of each experiment group for the duration of this experiment is shown in FIG. 3. As shown in FIG. 3, in the positive control group (Group II), decrease in body weight was seen on Day 1 and after due to the side effects of anticancer agent. In contrast, in groups administered with ALA (Group III, Group IV), decreased in body weight due to the side effects from anticancer agent was suppressed. Further, in groups administered with ALA (Group III, Group IV), re-increase of body weight was observed on Day 5 and after. Although the "full administration group" administered with ALA throughout the duration of experiment (Group IV) was the most effective, a certain effect was shown even in the "post-administration group" (Group III). Accordingly, reliable therapeutic and prophylactic effects by ALA administration were shown in regards to weight loss which is a side effect of anticancer agent.

Figure 4:
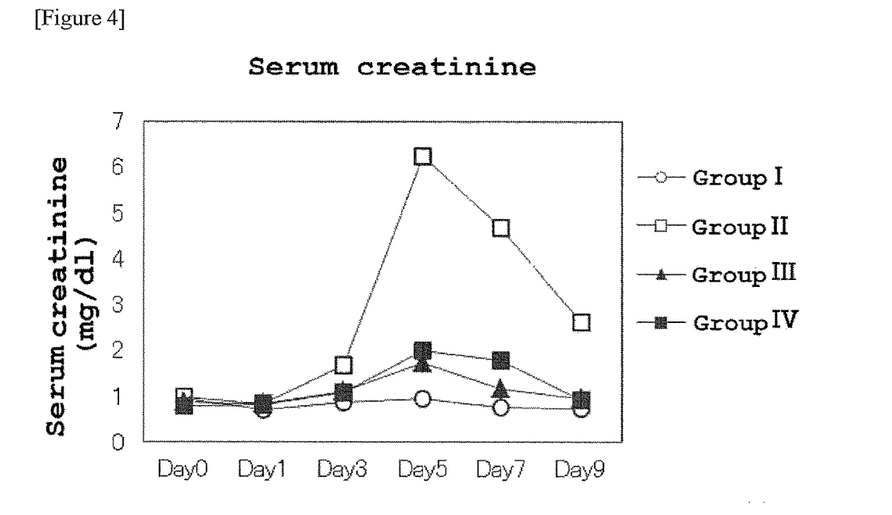
FIG. 4 is the graph showing the transition of serum creatinine according to administration conditions, when 6 weeks-old SD rats are administered cisplatin and ALA by 4 administration conditions.

The change in rat serum creatinine value of each experiment group for the duration of this experiment is shown in FIG. 4. As shown in FIG. 4, in the positive control group (Group II), a rapid increase in serum creatinine amount was seen on Day 3 and after due to the side effects of anticancer agent. On the other hand, in groups administered with ALA (Group III, Group IV), although serum creatinine value due to the side effects from anticancer agent showed slight increase on Day 5, a value not much different from the negative control group was maintained.

Figure 5:
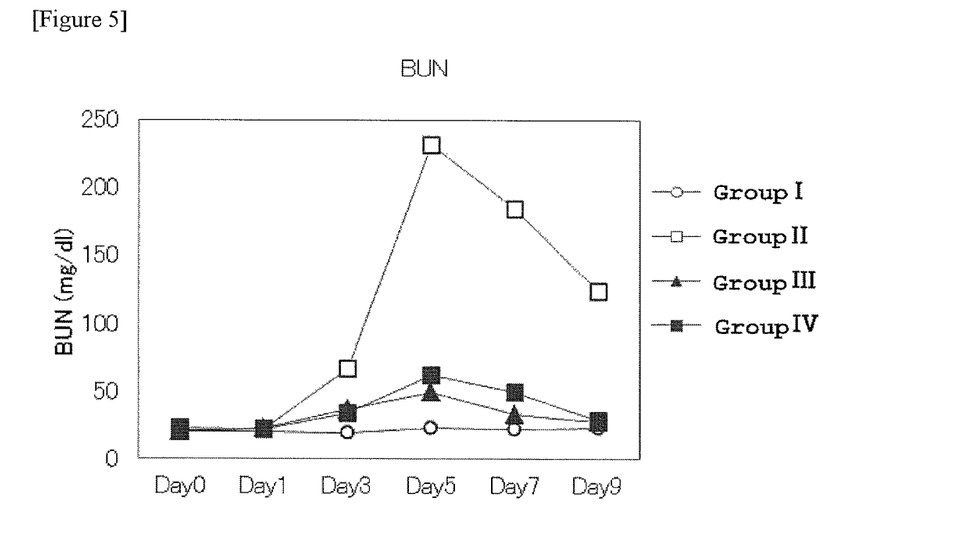
FIG. 5 is the graph showing the transition of urea nitrogen (BUN) according to administration conditions, when 6 weeks-old SD rats are administered cisplatin and ALA by 4 administration conditions.

The change in rat urea nitrogen value (BUN) of each experiment group for the duration of this experiment is shown in FIG. 5. As shown in FIG. 5, in the positive control group (Group II), a rapid increase in urea nitrogen value (BUN) was seen on Day 3 and after due to the side effects of anticancer agent. On the other hand, in groups administered with ALA (Group III, Group IV), it is shown that although urea nitrogen value due to the side effects from anticancer agent showed slight increase on Day 5, a value not much different from the negative control group was maintained.

Figure 6:
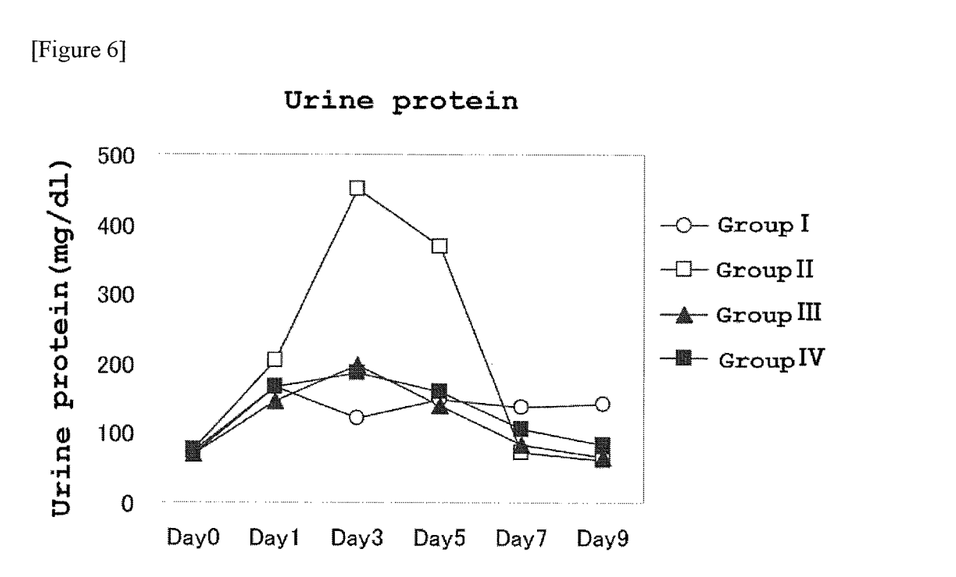
FIG. 6 is the graph showing the transition of urine protein value according to administration conditions, when 6 weeks-old SD rats are administered cisplatin and ALA by 4 administration conditions.

The change in rat urine protein value of each experiment group for the duration of this experiment is shown in FIG. 6. As shown in FIG. 6, in the positive control group (Group II), a rapid increase in urine protein value was seen on Day 1 and after due to the side effects of anticancer agent. On the other hand, in groups administered with ALA (Group III, Group IV), it is shown that although urine protein value due to the side effects from anticancer agent showed slight increase on Day 3 compared to the negative control group (Group I), a value not much different from the negative control group was maintained.

As apparent from FIGS. 4 to 6, ALA can alleviate kidney damage due to the side effects of anticancer agent.

Although the "full administration group" administered with ALA throughout the duration of experiment (Group IV) was the most effective, a certain effect was shown even in the "post-administration group" (Group III). Accordingly, reliable therapeutic and prophylactic effects by ALA administration were shown in regards to the side effects of anticancer agent on the kidney.

Figure 7:
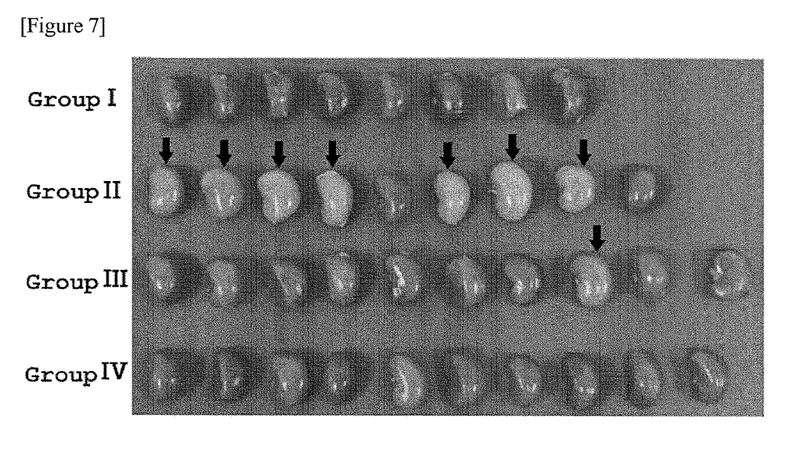
FIG. 7 is the image showing the kidney on Day 16 from the starting day of experiment, when 6 weeks-old SD rats are administered cisplatin and ALA by 4 administration conditions.

The photographic figure of the kidney of each rat resected on Day 16 is shown in FIG. 7. The kidneys of individuals that could be decided to have damage produced on renal function during the experimental period from serum creatinine value, urea toxin value (BUN), and urine protein value were yellow and edematized. The kidneys that were yellow and edematized are shown with arrows in FIG. 7.

Example 3: Influence of ALA Administration on Anticancer Effect of Anticancer Agent It was validated whether or not ALA administration has an influence on the cell toxicity (anticancer effect) of anticancer agent against cancer cells.

The following cancer cells were employed in this experiment: T24 cells (human transitional cell bladder cancer cells) and 253J-BV cells (human urinary tract epithelium cancer cells). Cisplatin was employed as the anticancer agent. ALA hydrochloride salt was employed as ALA. In addition, sodium ferrous citrate was administered together with ALA administration.

The concentrations of ALA and sodium ferrous citrate were concentrations that are about 3.35-folds higher (ALA hydrochloride salt: 200 µM, sodium ferrous citrate: 100 µM) than the concentrations where the effect of alleviating the side effects of anticancer agent was obtained in Examples 1 and 2 (ALA hydrochloride salt: 10 mg/kg of body weight (about 59.67 µM), sodium ferrous citrate: 15.7 mg/kg of body weight (about 29.85 µM)). Specifically, they were calculated so that the amounts of the concentration per 1 kg of body weight of ALA and sodium ferrous citrate in Example 3 are about 3.35-folds of the amounts of ALA and sodium ferrous citrate per 1 liter volume in Examples 1 and 2 (about 1.5-fold for cisplatin below was calculated similarly.).

On the other hand, the concentrations of cisplatin was a 2-fold dilution series with the maximum at about 1.5-folds of the concentration used in Examples 1 and 2 (8 mg/kg of body weight (about 26.66 µM)), which is 40 µM (40 µM, 20 µM, 10 µM, 5 µM, 2.5 µM, 1.25 µM, 0 µM).

Cell toxicity at each concentration was compared in the following Groups I to IV.

Group I: "No addition group," i.e. the group with no ALA administered

Group II: "Pre-administration group," i.e. the group with ALA administered only "during preculture"

Group III: "Simultaneous administration group," i.e. the group with ALA administered only "with cisplatin administration"

Group IV: "Full administration group," i.e. the group with ALA administered "during preculture" and "with cisplatin administration"

The meanings of each group will be further clearly described below.

Specifically, this experiment was performed as follows.
<Preculture>

(1) T24 cells (human transitional cell bladder cancer cells) or 253J-BV cells (human urinary tract epithelium cancer cells) were cultured with a 10 cm dish in DMEM medium comprising 10% FBS to a subconfluent state. They were then collected by trypsin treatment.

(2) For test groups Group I (no addition group) and Group III (simultaneous administration group), the cells collected in (1) were suspended to a density of 50000 cells/ml in DMEM medium comprising 10% FBS. For test groups Group II (pre-administration group) and Group IV (full administration group), the cells collected in (1) were suspended to a density of 50000 cells/ml in DMEM medium comprising 200 μM of ALA hydrochloride salt, 100 μM of sodium ferrous citrate, and 10% FBS.

(3) Next, each suspension obtained in (2) was dispensed in a 96-well microplate at 100 μl per well, and precultured at 37° C. for 24 hours.
<Cisplatin Administration>

(1) After preculture, the medium was removed from each well. DMEM medium comprising various concentrations (40, 20, 10, 5, 2.5, 1.25, 0 μM) of cisplatin and 10% FBS was added to Group I (no addition group) and Group II (pre-administration group), and cultured in a CO2 incubator at 37° C. In addition, DMEM medium containing various concentrations (40, 20, 10, 5, 2.5, 1.25, 0 μM) of cisplatin, 200 μM of ALA hydrochloride salt, and 100 μM of sodium ferrous citrate, and 10% FBS was added to Group III (simultaneous administration group) and Group IV (full administration group), and cultured in a CO2 incubator at 37° C.

(2) After culturing for 48 hours in the presence of cisplatin, 10 μl of WST-8 which is the substrate for Cell Counting Kit-8 (from Dojindo) was added to each well, and chromogenic reaction was allowed at 37° C. for 2 hours. The survival rate was then measured for each well by measuring the absorbance at 450 nm.

The absorbance of culturing in cisplatin-free medium was set at 100% survival rate. In addition, the absorbance of color development by adding WST-8 to cell-free medium was set at 0% survival rate. With this, "cell survival rate (%)" was calculated for each well. "Cell death rate (%)" was also calculated by the following formula.

"Cell death rate (%)"=100−"cell survival rate (%)"

Figure 8:
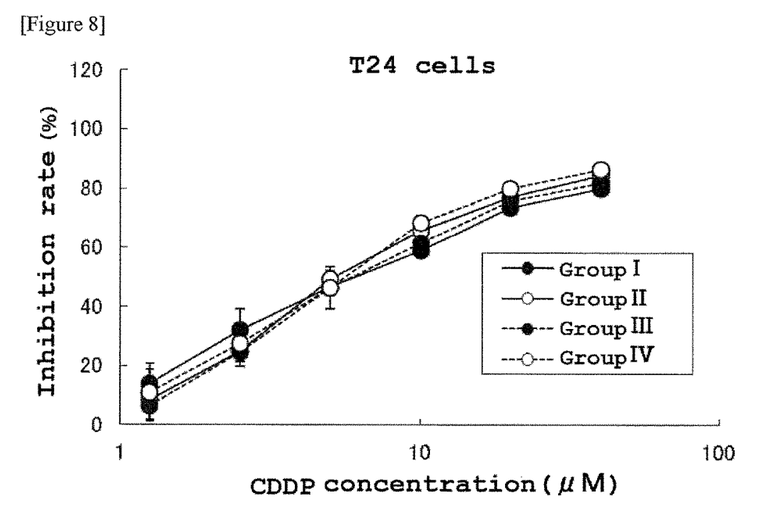
FIG. 8 is the graph showing the influence of administration of cisplatin and ALA to T24 cells (human transitional cell bladder cancer cells) on T24 cell survival.
Figure 9:
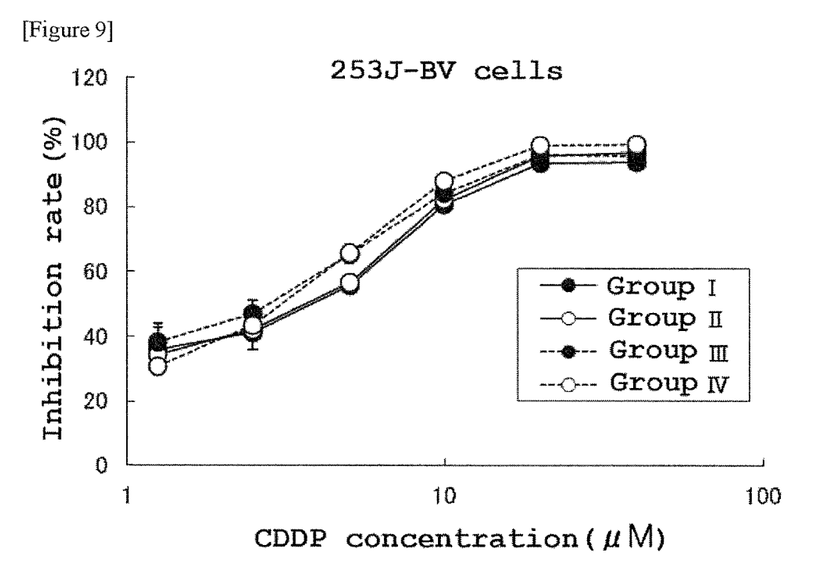
FIG. 9 is the graph showing the influence of administration of cisplatin and ALA to 253J-BV cells (human urinary tract epithelium cancer cells) on 253J-BV cell survival.

The cell death rate of Groups I to IV are shown in FIGS. 8 and 9. Since cell death is the inhibition of cell survival by cisplatin, "cell death rate (%)" is described as "inhibition rate (%)" in FIGS. 8 and 9.

FIG. 8 shows the death rate (%) of T24 cells (human transitional cell bladder cancer cells) due to cisplatin administration. The 50% inhibitory concentration (50% lethal concentration) (μM) of T24 cells in Groups I to IV were 5.73 μM (Group I), 5.21 μM (Group II), 4.87 μM (Group III), and 5.56 μM (Group IV), respectively.

FIG. 9 shows the death rate (%) of 253J-BV cells (human urinary tract epithelium cancer cells) due to cisplatin administration. The 50% inhibitory concentration (50% lethal concentration) (μM) of 253J-BV cells in Groups I to IV were 3.92 μM (Group I), 3.92 μM (Group II), 2.80 μM (Group III), and 2.89 μM (Group IV), respectively.

As shown in FIGS. 8 and 9, it was shown that ALA administration hardly attenuated the effect of anticancer agent on anticancer effect of cisplatin, regardless of its administration timing and administration duration.

Example 4: Influence of ALA Administration on Anticancer Effect of Anticancer Agent An emergency surgery was performed on a woman who developed intestinal obstruction in the advanced colon cancer on Aug. 19, 2009 (61-years old at the time). According to the observation at the time of surgery, there was colon cancer the size of a fist, and although the cancer was resected and the intestinal obstruction was cleared, numerous peritoneal metastases were seen and remaining life expectancy was declared at 3 months.

After the surgery, a molecular target drug such as Avastin was concomitantly used in addition to FOLFOX (triple-drug combination of 5-FU, Isovorin, and Elprat) and FOLFIRI (triple-drug combination of 5-FU, Isovorin, and Campto) as anticancer agent therapy. Further, 50 mg of aminolevulinic acid phosphate salt and 57.4 mg of sodium ferrous citrate per day were orally taken concurrently with this anticancer agent therapy.

As a result, it was possible to continue anticancer agent therapy for one year after the surgery. Administration of anticancer agent was given up after one year due to side effects, but oral intake of 50 mg of aminolevulinic acid phosphate salt and 57.4 mg of sodium ferrous citrate were continued, and she was able to survive for as long as one and a half years largely exceeding the declared 3 months life expectancy in a state with improved side effects.

Since the patient presented strong anemic symptom as a side effect, anemia improvement effect was selected as the comparison subject as the index of side effect improvement. The number of erythrocytes, hemoglobin value, and the number of leukocytes at (i) Aug. 19, 2009 which is just before the surgery and (ii) Jan. 28, 2011 which is about 1 year and 5 months after starting intake of aminolevulinic acid phosphate salt and sodium ferrous citrate are shown in Table 2 below.

TABLE 2

| | Number of Erythrocytes ($\times 10^6/\mu L$) | Hemoglobin (g/dL) | Number of Leukocytes ($\times 10^3/\mu L$) |
|---|---|---|---|
| Aug. 19, 2009 | 2.97 | 9.80 | 13.20 |
| Jan. 28, 2011 | 3.44 | 12.20 | 6.20 |

As recognized from the above Table, it is found that although decrease in the number of erythrocytes and hemoglobin as well as increase in leukocytes due to inflammation due to cancerous anemia were seen just before the surgery, the number of erythrocytes and hemoglobin are increased and anemia as a side effect of administration of anticancer agent is improved by administration of aminolevulinic acid phosphate salt and sodium ferrous citrate at about 1 year and 5 months after starting intake at (ii). On the other hand, the number of leukocytes settled at a normal value. It is thought that there was also strong damage on the hematopoiesis system considering the fact that strong side effects due to anticancer agent were shown, but the result that anemia is improved is astounding, and life with improved QOL could be spent for as long as one and a half years even while carrying peritoneal metastasis, which largely exceeds the doctor's life expectancy declared at 3 months.

INDUSTRIAL APPLICABILITY

The agent of the present invention can be advantageously utilized as a prophylactic and/or therapeutic agent for side effects of anticancer agent.

The invention claimed is:

1. A method for alleviating side effects of an anticancer agent in a subject, the method comprising administering the following (a) and (b) simultaneously or at different times to the subject in need thereof:
    (a) the anticancer agent; and
    (b) a prophylactic and/or therapeutic agent for alleviating side effects of the anticancer agent comprising a therapeutically effective amount of a compound shown by the following Formula (I) or a salt thereof, $$R^1\text{—NHCH}_2\text{COCH}_2\text{CH}_2\text{COOR}^2 \qquad (I)$$

wherein $R^1$ represents a hydrogen atom or an acyl group, and $R^2$ represents a hydrogen atom, a linear or branched alkyl group, a cycloalkyl group, an aryl group, or an aralkyl group, and wherein the prophylactic and/or therapeutic agent further comprises one or more metals.

2. The method according to claim 1, wherein said metal is selected from the group consisting of iron, magnesium, and zinc.

3. The method according to claim 1, wherein said side effect is at least one selected from the group consisting of a side effect related to kidney, a side effect related to skin symptoms, a side effect related to general symptoms, and a side effect related to gastrointestinal system.

4. The method according to claim 1, wherein the prophylactic and/or therapeutic agent is administered simultaneously with the anticancer agent.

* * * * *